United States Patent
Fang et al.

(10) Patent No.: US 12,008,313 B2
(45) Date of Patent: Jun. 11, 2024

(54) MEDICAL DATA VERIFICATION METHOD AND ELECTRONIC DEVICE

(71) Applicant: BAIDU INTERNATIONAL TECHNOLOGY (SHENZHEN) CO., LTD., Shenzhen (CN)

(72) Inventors: Zhou Fang, Shenzhen (CN); Yabing Shi, Shenzhen (CN); Ye Jiang, Shenzhen (CN); Chunguang Chai, Shenzhen (CN)

(73) Assignee: BAIDU INTERNATIONAL TECHNOLOGY (SHENZHEN) CO., LTD., Guangdong (CN)

( * ) Notice: Subject to any disclaimer, the term of this patent is extended or adjusted under 35 U.S.C. 154(b) by 347 days.

(21) Appl. No.: 17/448,065

(22) Filed: Sep. 20, 2021

(65) Prior Publication Data
US 2022/0004706 A1    Jan. 6, 2022

(30) Foreign Application Priority Data
Sep. 29, 2020    (CN) .......................... 202011053052.7

(51) Int. Cl.
*G06F 40/194*    (2020.01)
*G06F 16/33*    (2019.01)
(Continued)

(52) U.S. Cl.
CPC ........ *G06F 40/194* (2020.01); *G06F 16/3347* (2019.01); *G06F 16/367* (2019.01);
(Continued)

(58) Field of Classification Search
CPC .... G06F 40/30; G06F 40/194; G06F 16/3347; G06F 16/367; G16H 50/70
See application file for complete search history.

(56) References Cited

U.S. PATENT DOCUMENTS

| | | | |
|---|---|---|---|
| 6,240,408 B1* | 5/2001 | Kaufman | G06F 16/3344 |
| | | | 707/999.005 |
| 2012/0296637 A1* | 11/2012 | Smiley | G06F 18/22 |
| | | | 704/9 |

(Continued)

FOREIGN PATENT DOCUMENTS

| | | |
|---|---|---|
| CN | 110390003 A | 10/2019 |
| CN | 111259112 A | 6/2020 |

(Continued)

OTHER PUBLICATIONS

Soğnciğlu et al., "BIOSSES: a semantic sentence similarity estimation system for the biomedical domain." Bioinformatics 33.14 (2017): i49-i58 (Year: 2017).*

(Continued)

*Primary Examiner* — Samuel G Neway
(74) *Attorney, Agent, or Firm* — Lippes Mathias LLP (57) ABSTRACT

The present disclosure provides a medical data verification method, apparatus and an electronic device, related to a field of artificial intelligence technologies, such as AI (artificial intelligence) medical treatment, deep learning, knowledge graphs, natural language processing. A specific implementation is: obtaining medical data to be verified and a candidate document; obtaining feature vectors respectively corresponding to the medical data to be verified and the candidate document by processing the medical data to be verified and the candidate document by using a nature language processing model; obtaining N correlation vectors by calculating correlation between the medical data to be verified and the candidate document based on the feature vectors by using N methods, N being a positive integer greater than 1; and determining a confidence degree of the medical data to be verified to the candidate document by performing fusion calculation on the N correlation vectors.

14 Claims, 4 Drawing Sheets

(51) Int. Cl.
  *G06F 16/36* (2019.01)
  *G06F 16/93* (2019.01)
  *G06F 40/205* (2020.01)
  *G06F 40/30* (2020.01)
  *G06N 3/08* (2023.01)
  *G16H 10/60* (2018.01)
  *G16H 40/20* (2018.01)
  *G16H 50/20* (2018.01)
  *G16H 50/70* (2018.01)

(52) U.S. Cl.
  CPC ............ *G06F 16/93* (2019.01); *G06F 40/205* (2020.01); *G06F 40/30* (2020.01); *G16H 50/20* (2018.01); *G16H 50/70* (2018.01); *G06N 3/08* (2013.01); *G16H 10/60* (2018.01); *G16H 40/20* (2018.01)

(56) References Cited

U.S. PATENT DOCUMENTS

| | | | | |
|---|---|---|---|---|
| 2015/0347393 | A1* | 12/2015 | Futrell | G06F 40/30 704/9 |
| 2016/0196258 | A1* | 7/2016 | Ma | G06F 40/51 704/8 |
| 2017/0193197 | A1* | 7/2017 | Randhawa | G16H 10/60 |
| 2018/0225553 | A1* | 8/2018 | Ha | G06Q 10/067 |
| 2019/0065506 | A1* | 2/2019 | Li | G06N 3/042 |
| 2019/0155898 | A1* | 5/2019 | Li | G06F 40/211 |
| 2020/0104631 | A1* | 4/2020 | Zhang | G06F 40/30 |
| 2020/0104746 | A1* | 4/2020 | Strope | G06N 5/04 |
| 2020/0210466 | A1 | 7/2020 | Yin et al. | |
| 2020/0242140 | A1* | 7/2020 | Xu | G06N 3/08 |
| 2021/0217504 | A1* | 7/2021 | Fang | G06F 40/30 |
| 2022/0004706 | A1* | 1/2022 | Fang | G16H 50/70 |
| 2022/0374601 | A1* | 11/2022 | Kim | G06F 40/289 |

FOREIGN PATENT DOCUMENTS

| | | |
|---|---|---|
| CN | 111259663 A | 6/2020 |
| CN | 111626817 A | 9/2020 |
| CN | 111640511 A | 9/2020 |
| JP | 2011129997 A1 | 6/2011 |
| JP | 2019049954 A | 3/2019 |
| KR | 102114267 B1 | 5/2020 |

OTHER PUBLICATIONS

Office Action for Korean Patent Application No. 10-2021-0128335, dated Jul. 26, 2023, 10 pages.
Office Action for Chinese Patent Application No. 202011053052.7, dated Jul. 9, 2023, 20 pages.
Office Action for Japanese Application No. 2021-154386, dated Nov. 8, 2022, 4 pages.
Extended European Search Report for Application No. 21198346.5, dated Mar. 2, 2022, 9 pages.
Tao Zheng et al., "Detection of Medical Text Semantic Similarity Based on Convolutional Neural Network", BMC Medical Informatics and Decision Making, Aug. 7, 2019, 11 pages.
Yanshan Wang et al., "MedSTS: a resource fro clinical semantic textual similarity", Lang Resources & Evaluation, Oct. 24, 2018, 16 pages.
The Wayback Machine—https://web.archive.org/web/20200310203643/ https://investigate.ai/t . . . , "Conceptual documents similarity with word embeddings", Mar. 10, 2020, 11 pages.

* cited by examiner

MEDICAL DATA VERIFICATION METHOD AND ELECTRONIC DEVICE

CROSS-REFERENCE TO RELATED APPLICATION

This application claims priority to and benefits of Chinese Patent Application Serial No. 202011053052.7, filed with the State Intellectual Property Office of P. R. China on Sep. 29, 2020, the entire content of which is incorporated herein by reference.

FIELD

The present disclosure relates to a field of computer technologies, and particularly to a field of artificial intelligence technologies, and more particularly to a medical data verification method and an electronic device.

BACKGROUND

Medical data verification technologies can be used to assist in constructing medical atlases. For example, in the process of constructing a medical atlas, the acquired medical data can be verified to determine the degree of confidence of the medical data, and supporting evidence is given, and then the medical data with a higher degree of confidence and its corresponding supporting evidence are associated with each other and stored in the medical atlas as a piece of medical atlas data to enrich and expand the content of the and improve the accuracy of the medical atlas data.

With the development of technologies such as artificial intelligence, deep learning, natural language processing, the verification of medical data can be implemented through deep learning models. For example, multiple deep learning models connected in series may be trained by designing a structure of multiple deep learning model connected in series and using large-scale annotation data, and then the degree of confidence of medical data is verified by using the trained multiple deep learning models connected in series based on the basic characteristics of the medical data.

SUMMARY

According to embodiments of the present disclosure, a medical data verification method is provided. The method includes: obtaining medical data to be verified and a candidate document; obtaining feature vectors respectively corresponding to the medical data to be verified and the candidate document by processing the medical data to be verified and the candidate document by using a nature language processing model; obtaining N correlation vectors by calculating correlation between the medical data to be verified and the candidate document based on the feature vectors by using N methods, N being a positive integer greater than 1; and determining a confidence degree of the medical data to be verified to the candidate document by performing fusion calculation on the N correlation vectors.

According to embodiments of the present disclosure, an electronic device is provided. The electronic device includes at least one processor; and a memory communicatively couple to the at least one processor. The memory has instructions executable by the at least one processor stored thereon that, when executed by the at least one processor, cause the at least one processor to perform the foregoing medical data verification method.

According to embodiments of the present disclosure, a non-transitory computer-readable storage medium having computer instructions stored thereon is provided. The computer instructions are configured to cause a computer to perform the foregoing medical data verification method.

It is to be understood that the content described in this section is not intended to identify the key or important features of the embodiments of the present disclosure, nor is it intended to limit the scope of the present disclosure. Other features of the present disclosure will be easily understood through the following description.

BRIEF DESCRIPTION OF THE DRAWINGS

The drawings are for better understanding of the present disclosure and do not constitute a limitation to the present disclosure, in which.

DETAILED DESCRIPTION

The exemplary embodiments of the present disclosure are described below with reference to the accompanying drawings, which include various details of the embodiments of the present disclosure to facilitate understanding, and should be regarded as merely exemplary. Therefore, those skilled in the art should appreciate that various changes and modifications can be made to the embodiments described herein without departing from the scope and spirit of the present disclosure. Likewise, for clarity and conciseness, descriptions of well-known functions and structures are omitted in the following description.

The technical fields involved in the solution of the present disclosure are briefly described below.

Artificial intelligence (AI) is a subject that studies using computers to simulate certain human thinking processes and intelligent behaviors, such as learning, reasoning, thinking, planning, etc., involving both hardware-level technologies and software-level technologies. Artificial intelligence hardware technologies generally include directions such as computer vision technologies, speech recognition technologies, natural language processing technologies, machine learning/deep learning, big data processing technologies, and knowledge graph technologies.

AI medical treatment applies, based on the Internet, artificial intelligence technology and big data services to the medical industry through the construction of infrastructure and data collection to improve the diagnostic efficiency and service quality of the medical industry, and to better solve problem of medical resource shortage and population aging. AI medical treatment can be simplified to "artificial intelligence+medical treatment", which is the empowering phenomenon of the artificial intelligence technology for application scenarios in medical-related fields. Specifically, AI is suitable for medical imaging diagnosis, chronic disease management and lifestyle guidance, disease investigation and pathology research, medicinal development and other fields, and it helps to fill the gap between genotype and phenotype in precision medicine.

Deep learning is a new research direction in the field of machine learning. It has been introduced into machine learning to bring it closer to the original goal, i.e., artificial intelligence. Deep learning is to learn the internal rules and representation levels of sample data. The information obtained in the learning process is of great help to the interpretation of data such as text, images and sounds. Its ultimate goal is to enable machines to have the ability to analyze and learn like humans, and to recognize data such as text, images, and sounds. Deep learning achieves many results in search technologies, data mining, machine learning, machine translation, natural language processing, multimedia learning, speech, recommendation and personalization technologies, and other related fields.

Knowledge graph, known as a knowledge domain visualization or knowledge domain mapping map in the field of library and intelligence community, is a series of various graphs showing the knowledge development processes and structure relationships. Visualization technology is used to describe knowledge resources and their carriers, mining, analyzing, constructing, drawing and displaying knowledge and their interrelationships. The knowledge map combines the theories and methods of applied mathematics, graphics, information visualization technology, information science and other disciplines with methods such as metrological citation analysis, co-occurrence analysis, and uses the visual map to vividly display the core structure, development history, frontier fields and overall knowledge structure of a discipline, that develops history, to achieve the modern theory of the purpose of multi-disciplinary integration.

Natural language processing is an important direction in the field of computer science and artificial intelligence. It studies various theories and methods that can realize effective communication between humans and computers in natural language. Natural language processing is a science that integrates linguistics, computer science, and mathematics. Therefore, research in this field may involve natural language, i.e., the language daily used by people, so it is closely related to the research of linguistics, but there are important differences. Natural language processing is not the general study of natural language, but developing a computer system that can effectively realize natural language communication, especially the software system. Therefore, it is part of computer science.

For the problem of poor accuracy in the method of verifying medical data through multiple deep learning models connected in series in the related art, embodiments of the present disclosure propose a medical data verification method.

A medical data verification method and apparatus, an electronic device, and a storage medium provided in the present disclosure are described in detail below with reference to the drawings.

Figure 1:
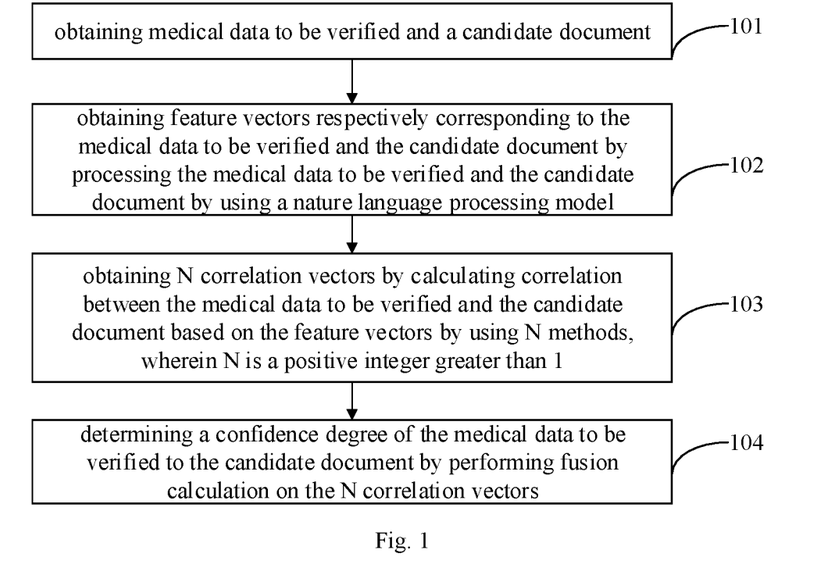
FIG. 1 is a flow chart of a medical data verification method according to an embodiment of the present disclosure.

FIG. 1 is a flow chart of a medical data verification method according to an embodiment of the present disclosure.

As illustrated in FIG. 1, the medical data verification method includes followings.

At block 101, medical data to be verified and a candidate document are obtained.

It may be noted that, the medical data verification method according to embodiments of the present disclosure may be executed by a medical data verification apparatus according to embodiments of the present disclosure. The medical data verification apparatus according to embodiments of the present disclosure may be configured in any electronic device to execute the medical data verification method according to embodiments of the present disclosure.

The medical data to be verified may refer to medical facts whose accuracy needs to be verified currently.

The candidate document may be authoritative medical content collected and stored in advance, such as medical books, medical papers, etc., or fragments from medical books, medical papers, etc.

In some embodiments of the present disclosure, different ways may be used to obtain the medical data to be verified and the candidate document for different application scenarios. Alternatively, when the medical data verification method according to the present disclosure is applied in an offline scenario, a large amount of diagnostic data made during diagnosing by doctors can be captured in advance from the network or medical information systems of various medical institutions to form the medical data set to be verified, and one piece of medical data is obtained from the medical data set to be verified each time as the medical data to be verified. In addition, medical-related documents are captured from various documents and thesis databases in advance to form a document set. And then, all documents in the document set may be used as candidate documents when the medical data to be verified is obtained. Alternatively, the medical data to be verified may be used as a keyword to search in the document set, to obtain one or more documents related to the medical data to be verified from the document set as the candidate documents.

Alternatively, when the medical data verification method of the embodiment of the present disclosure is applied in an online scenario, such as an auxiliary diagnosis system of a medical institution, medical-related documents may be captured from various documents and thesis databases in advance to form a document set, and then stored in a sever of a medical information system of a medical institution. The server may obtain the diagnosis data made by a doctor in real time from a client side of the doctor as the medical data to be verified. And then all documents in the document set may be used as candidate documents when the medical data to be verified is obtained. Alternatively, the medical data to be verified may be used as a keyword to search in the document set, to obtain one or more documents related to the medical data to be verified from the document set as the candidate documents.

At block 102, feature vectors respectively corresponding to the medical data to be verified and the candidate document are obtained by processing the medical data to be verified and the candidate document by using a nature language processing model.

The nature language processing model may be an ERMIE (enhanced representation from knowledge integration) model, a BERT (bidirectional encoder representation from transformer) model, etc. In actual use, a suitable natural language processing model can be selected, which is not limited in the embodiments of the present disclosure.

It should be noted that, a large amount of medical knowledge can be extracted from a medical knowledge base in advance, and the natural language processing model may be pre-trained by using the extracted large amount of medical knowledge to improve the recognition performance of the natural language processing model in medical industry scenarios.

Figure 2:
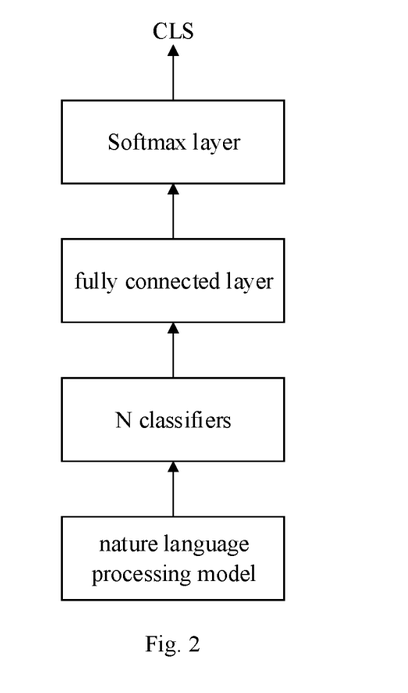
FIG. 2 is a structural diagram of a classification model according to an embodiment of the present disclosure.

In some embodiments of the present disclosure, a deep learning model may be constructed to realize the verification of medical data through the deep learning model. For example, a classification model may be designed based on a deep learning model of the PaddlePaddle deep learning computing framework. The model structure is shown in FIG. 2, including a natural language processing model, N classifiers corresponding to N calculation methods, a fully connected layer, and a softmax layer. CLS is a confidence degree output by the classification model.

In some embodiments of the present disclosure, the medical data to be verified and the candidate document may be input into the natural language processing model, so that the natural language processing model separately recognizes the medical data to be verified and the candidate document. For example, word segmentation processing may be separately performed on the medical data to be verified and the candidate document first, to determine basic units included in the medical data to be verified and basic units included in the candidate document. And then, the vector representation corresponding to each basic unit included in the medical data to be verified is determined, that is, respective feature vectors corresponding to the medical data to be verified are determined. Vector representation corresponding to each basic unit included in the candidate document is determined, that is, respective feature vectors corresponding to the candidate document are determined.

It should be noted that, the basic unit may be any granularity of characters, words, and phrases, and is related to the working principle of the natural language processing model, which is not limited in the embodiment of the present disclosure.

At block 103, N correlation vectors are obtained by calculating correlation between the medical data to be verified and the candidate document based on the feature vectors by using N methods, N is a positive integer greater than 1.

The correlation vector refers to a vector that can represent a degree of relevance between the medical data to be verified and the candidate document.

In some embodiments of the present disclosure, a variety of calculation methods may be used to calculate the relevance between the medical data to be verified and the candidate document, so as to improve the accuracy of the representation of the relevance between the medical data to be verified and the candidate document, thereby improving the accuracy of medical data verification.

As a possible implementation, the feature vectors corresponding to the medical data to be verified may be first integrated to generate a first feature matrix corresponding to the medical data to be verified, and the feature vectors corresponding to the candidate document may be integrated to generate a second feature matrix corresponding to the candidate document. After that, N methods are used to perform calculation on the first feature matrix and the second feature matrix, and a calculation result corresponding to each method is determined as a correlation vector.

It should be noted that, in actual use, the N methods may include N of a softmax operation, a subtraction operation, a cosine operation, a sine operation, a tangent operation, an addition operation, a multiplication operation, a division operation, and other operations, which is not limited in embodiments of the present disclosure.

It should be noted that, if a calculation result of a certain method performed on the first feature matrix and the second feature matrix is still a matrix, transformation may be performed on the obtained matrix, to transform the obtained matrix into a vector form, thereby generating a correlation vector calculated in the certain method. For example, the obtained matrix may be transformed into a correlation vector by performing a summing operation or an averaging operation on elements of each row or elements of each column of the obtained matrix.

For example, the medical data to be verified contains m characters, and each corresponding feature vector is an n-dimensional row vector. The candidate document contains k characters, and each corresponding feature vector is an n-dimensional row vector. The value of N is 3, and the N methods are the softmax operation, the subtraction operation, and the cosine operation. Then, the dimension of the first feature matrix corresponding to the medical data to be verified is m×n, and the dimension of the second feature matrix corresponding to the candidate document is k×n. And then, each of the softmax operation, the subtraction operation, and the cosine operation are performed on the first feature matrix and the second feature matrix to generate 3 correlation vectors between the medical data to be verified and the candidate document.

At block 104, a confidence degree of the medical data to be verified to the candidate document is determined by performing fusion calculation on the N correlation vectors.

In some embodiments of the present disclosure, after the N correlation vectors between the medical data to be verified and the candidate document are determined, the fusion calculation is performed on the N correlation vectors through a fully connected layer in a classification model, and classification processing is performed based on a fusion result of the N correlation vectors through the softmax layer, to output the confidence degree of the medical data to be verified to the candidate document. In detail, the greater the confidence degree is, the greater the probability that the candidate document is used as supporting evidence to prove that the medical data to be verified is reliable. Conversely, it indicates that the probability that the candidate document is used as supporting evidence to prove that the medical data to be verified is reliable is small.

As a possible implementation, in a scenario of constructing a medical atlas, after the confidence degree of the medical data to the candidate document is determined, when the confidence degree of the medical data to be verified is greater than or equal to a confidence threshold, it may be determined that the medical data to be verified is valid, and the corresponding candidate document is stored in association with the medical data to be verified to expand the medical atlas.

It should be noted that, if there are multiple candidate documents corresponding to the medical data to be verified, when a confidence degree of the medical data to be verified to any one of the multiple candidate documents is greater than or equal to the confidence threshold, it is determined that the medical data to be verified is valid, and a candidate document that corresponding to a maximum confidence degree of the medical data to be verified is stored in association with the medical data to be verified, so as to expand the medical atlas.

With the technical solution according to embodiments of the present disclosure, the feature vectors respectively corresponding to the medical data to be verified and the candidate document are obtained by processing the medical data to be verified and the candidate document by using the nature language processing model, multiple correlation vectors are obtained by using multiple methods to calculate the correlation between the medical data to be verified and the candidate document based on the obtained feature vectors, and then, fusion calculation is performed on the correlation vectors to determine the confidence degree of the medical data to the candidate document. Thus, through an end-to-end deep learning model, the correlation between medical data and the candidate document is calculated by using multiple methods, so that the correlation and difference between the medical data and the candidate document are accurately represented from multiple dimensions, and the end-to-end model may avoid accumulation of errors, thus improving the accuracy of medical data verification.

In a possible implementation of the present disclosure, the medical data to be verified may be represented in a form of SPO triples, where S represents an entity, P represents an attribute, and O represents an attribute value. It is determined whether the medical data to be verified is valid based on a correlation between a candidate evidence and each of S, P, and O and, thus further improving the accuracy of medical data verification.

The medical data verification method provided in the embodiments of the present disclosure will be further described below with reference to FIG. 3.

Figure 3:
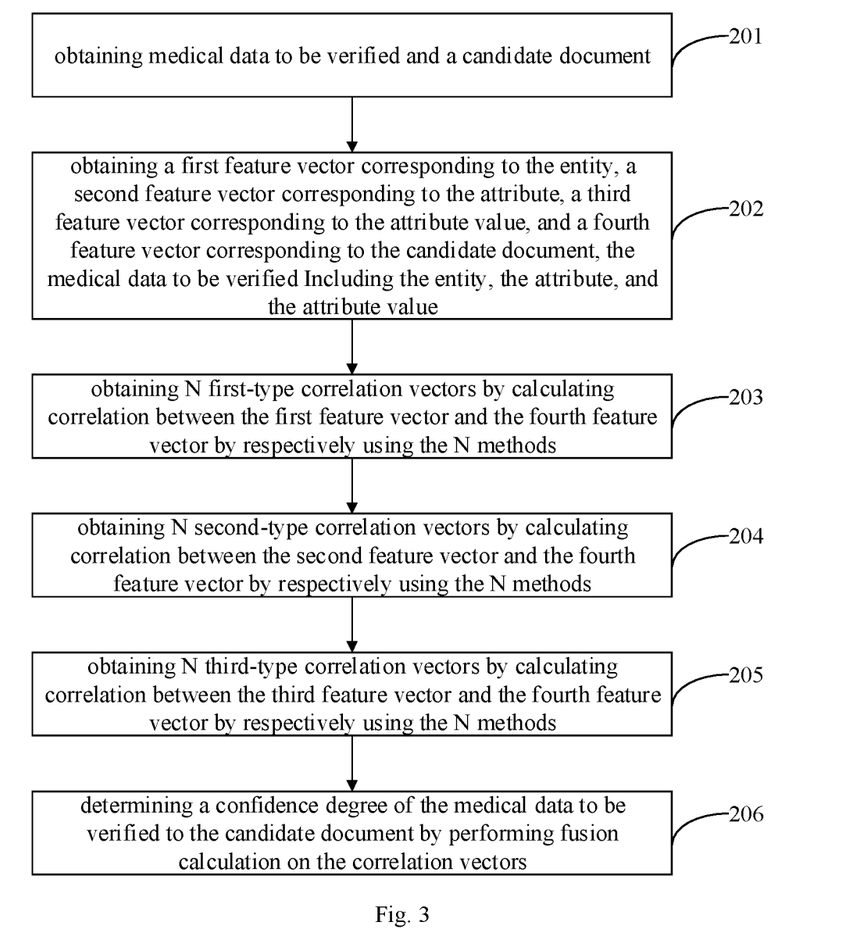
FIG. 3 is a flow chart of a medical data verification method according to an embodiment of the present disclosure.

FIG. 3 is a flow chart of a medical data verification method according to an embodiment of the present disclosure.

As illustrated in FIG. 3, the medical data verification method includes followings.

At block 201, medical data to be verified and a candidate document are obtained.

For the detailed implementation process and principle of step 201, reference may be made to the detailed description of the foregoing embodiment, which will not be repeated here.

At block 202, the medical data to be verified and the candidate document are processed by using a nature language processing model to obtain a first feature vector corresponding to an entity included in the medical data to be verified, a second feature vector corresponding to an attribute included in the medical data to be verified, a third feature vector corresponding to an attribute value included in the medical data to be verified, and a fourth feature vector corresponding to the candidate document. The medical data includes the entity, the attribute and the attribute value.

In some embodiments of the present disclosure, each piece of medical data to be verified may be represented in a form of a SPO triple, where S represents an entity, P represents an attribute, and O represents an attribute value. The entity may refer to a specific disease, the attribute may include at least one of a clinical features, etiology and pathology, examination and inspection, recommended surgery, treatment plan, recommended medication, drug effect, and complication. The attribute value refers to a specific value of a corresponding attribute. For example, the medical data is <measles, symptom, skin maculopapule>, thus the entity S is measles, the attribute P is the symptom, and the attribute value O is the skin maculopapule.

In some embodiments of the present disclosure, if the representation form of the medical data to be verified is the SPO triple, the medical data to be verified and the candidate document may be input to the nature language processing model in a form of "S[SEP]P[SEP]O[SEP]PARA", so that, the nature language processing model may separately process the entity, the attribute and the attribute value in the medical data to be verified and the candidate document, the vector representation of the entity, the attribute, the attribute value and the candidate document, i.e., the first feature vector corresponding to the entity, the second feature vector corresponding to the attribute, the third feature vector corresponding to the attribute value, and the fourth feature vector corresponding to the candidate document. PARA is the candidate document, [SEP] is a separator.

It should be noted that, when the nature language processing model divides each of the entity, the attribute, the attribute value and the candidate document into multiple base units for processing, so as to generate a vector representation corresponding to each base unit, each of the first feature vector, the second feature vector, the third feature vector and the fourth feature vector may consist of multiple vector representation. That is, the representation forms of the first feature vector, the second feature vector, the third feature vector and the fourth feature vector may be matrixes.

Further, there is strong dependencies between the entity and the attribute, and between the attribute and the attribute value of the medical data, therefore, a vector representation corresponding to the SP and a vector representation corresponding to OP, so as to improve the accuracy of representing the medical data. In other words, in a possible implementation of embodiments of the present disclosure, the above method may further include the following.

At least one of a fifth feature vector corresponding to the entity and the attribute, a sixth feature vector corresponding to the attribute and the attribute value, and a seventh feature vector corresponding to the entity and the attribute value is obtained.

In some embodiments of the present disclosure, pre-training may be performed for the nature language processing model, so that the nature language processing model may determine at least one of the fifth feature vector, the sixth feature vector and the seventh feature vector based on the entity, the attribute and the attribute value of the inputted medical data. Thus, the medical data to be verified may be described comprehensively and completely in multiple aspects such as the relationship between the entity and the attribute, the relationship between the attribute and the attribute value, and the relationship between the entity and the attribute value.

As a possible implementation, for the medical data, the relationship information between the entity and the attribute and the relationship information between the attribute and the attribute value may be cared, thus the fifth feature vector corresponding to the entity and the attribute and the sixth feature vector corresponding to the attribute and the attribute value are generated through the nature language processing model.

At block 203, N first-type correlation vectors are obtained by calculating correlation between the first feature vector and the fourth feature vector by respectively using N methods.

In some embodiments of the present disclosure, after the vector representations of the medical data to be verified and the candidate document through the nature language processing model, the correlation between the entity and the candidate document, the correlation between the attribute and the candidate document, and the correlation between the attribute value and the candidate document may be respectively determined, so that the correlation between the medical data to be verified and the candidate document is described in multiple dimensions, thus further improving the accuracy of medical data verification.

As a possible implementation, the N methods may be used to perform calculation on the first feature vector and the fourth feature vector first, and a calculation result corresponding to each method is determined as a first-type correlation vector, which is used to represent the correlation between the entity and the candidate document.

At block 204, N second-type correlation vectors are obtained by calculating correlation between the second feature vector and the fourth feature vector by respectively using the N methods.

In some embodiments of the present disclosure, the N methods may be respectively used to perform calculation on the second feature vector and the fourth feature vector, and a calculation result corresponding to each method is determined as one second-type correlation vector, which is used to represent the correlation between the attribute and the candidate document.

At block 205, N third-type correlation vectors are obtained by calculating correlation between the third feature vector and the fourth feature vector by respectively using the N methods.

In some embodiments of the present disclosure, the N methods may be respectively used to perform calculation on the third feature vector and the fourth feature vector, and a calculation result corresponding to each method is determined as one third-type correlation vector, which is used to represent the correlation between the attribute value and the candidate document.

It should be noted that, the N method in the embodiments of the present disclosure may be the same as the operations described in the above embodiments, and the detailed implementation process and principle of determining the first-type correlation vectors, the second-type correlation vectors, and the third-type correlation vectors may refer to the detailed description of the above embodiments and will not be repeated here.

Further, if the fifth feature vector corresponding to the entity and the attribute, the sixth feature vector corresponding to the attribute and the attribute value, and the seventh feature vector corresponding to the entity and the attribute value are generated through the nature language processing model in the foregoing steps, the following may be performed. N methods may be used to perform calculation on the fifth feature vector and the fourth feature vector, and a calculation result corresponding to each method is determined as a fifth-type correlation vector, which is used to represent the correlation between the SP and the candidate document. N methods may be used to perform calculation on the sixth feature vector and the fourth feature vector, and a calculation result corresponding to each method is determined as a sixth-type correlation vector, which is used to represent the correlation between the PO and the candidate document. N methods may be used to perform calculation on the seventh feature vector and the fourth feature vector, and a calculation result corresponding to each method is determined as a seventh-type correlation vector, which is used to represent the correlation between the SO and the candidate document.

At block 206, a confidence degree of the medical data to be verified to the candidate document is determined by performing fusion calculation on the correlation vectors.

In some embodiments of the present disclosure, after the respective types of correlation vectors between the SPO triple corresponding to the medical data to be verified and the candidate document are determined, the fusion calculation is performed on the respective types of correlation vectors through a fully connected layer, to generated the confidence degree of the medical data to be verified to the candidate document.

As a possible implementation, the fusion calculation may be performed on each correlation vector to determine the correlation between the candidate document and each of the entity, the attribute, and the attribute value respectively. That is, in a possible implementation of the embodiments of the present disclosure, the above 206 may include the following.

A first fusion vector is obtained by fusing the N first-type correlation vectors.

A second fusion vector is obtained by fusing the N second-type correlation vectors.

A third fusion vector is obtained by fusing the N third-type correlation vectors.

The confidence degree of the medical data to be verified to the candidate document is determined by performing fusion calculation on the first fusion vector, the second fusion vector and the third fusion vector.

In some embodiments of the present disclosure, the N first-type correlation vectors may be spliced to generate the first fusion vector. Alternatively, a sum of the N first-type correlation vectors may be determined as the first fusion vector. Alternatively, a mean value of the N first-type correlation vectors may be determined as the first fusion vector. Alternatively, the N first-type correlation vectors may be given corresponding weights according to importance of the N first-type correlation vectors, and a weighted sum of the N first-type correlation vectors is determined as the first fusion vector.

Correspondingly, fusion processing may be respectively performed on the N second-type correlation vectors and the N third-type correlation vectors by using the same way to generate the second fusion vector and the third fusion vector, which is not repeated here.

It should be noted that, the method for fusing the first-type correlation vectors, the second-type correlation vectors, and the third-type correlation vectors may include but not is not limited to the above examples. In actual application, the method for performing the fusion processing on the respective types of correlation vectors may be determined according to the actual needs and specific application scenarios, which is not limited in embodiments of the present disclosure.

In some embodiments of the present disclosure, the first fusion vector may reflect the overall correlation between the entity in the medical data to be verified and the candidate document, the second fusion vector may reflect the overall correlation between the attribute in the medical data to be verified and the candidate document, and the third fusion vector may reflect the overall correlation between the attribute value in the medical data to be verified and the candidate document, therefore, the fusion calculation may be performed on the first fusion vector, the second fusion vector and the third fusion vector through the softmax layer in the classification model to generate the overall correlation between the medical data to be verified and the candidate document, i.e., the confidence degree of the medical data to be verified to the candidate document.

It may be understood that, if N fifth-type correlation vectors, N sixth-type correlation vectors or N seventh-type correlation vectors are generated in the foregoing steps, the fusion processing may further performed on the N fifth-type correlation vectors, the N sixth-type correlation vectors and the N seventh-type correlation vectors based on the above methods to generate a fifth fusion vector, a sixth fusion vector, and a seventh fusion vector. And then, the fusion calculation is performed on the first fusion vector, the second fusion vector, the third fusion vector, the fifth fusion vector, the sixth fusion vector and the seventh fusion vector to determine the confidence degree of the medical data to be verified, when based on the candidate document.

As another possible implementation, the various correlation vectors may be fused directly, so that the overall correlation degree between the medical data to be verified and the candidate document may be represented by the vector obtained through the fusion. That is, in a possible implementation of embodiments of the present disclosure, the method may further include the following.

The N first-type correlation vectors, the N second-type correlation vectors and the N third-type correlation vectors are fused to generate a fourth fusion vector.

The confidence degree of the medical data to be verified to the candidate document is determined by performing calculation on the fourth fusion vector.

In some embodiments of the present disclosure, the N first-type correlation vectors, the N second-type correlation vectors and the N third-type correlation vectors may be spliced to generate the fourth fusion vector. Alternatively, a sum of the N first-type correlation vectors, the N second-type correlation vectors and the N third-type correlation vectors may be determined as the fourth fusion vector. Alternatively, a mean value of the N first-type correlation vectors, the N second-type correlation vectors and the N third-type correlation vectors may be determined as the fourth fusion vector. Alternatively, the first-type correlation vector, the second-type correlation vector and the third-type correlation vector may be given corresponding weights according to importance of the correlations between the entity and the candidate document, between the attribute and the candidate document, and between the attribute value and the candidate document, and a weighted sum of the N first-type correlation vectors, the N second-type correlation vectors and the N third-type correlation vectors may be determined as the fourth fusion vector.

It should be noted that, the method for fusing the first-type correlation vectors, the second-type correlation vectors, and the third-type correlation vectors may include but not is not limited to the above examples. In actual application, the method for performing the fusion processing on the correlation vectors may be determined according to the actual needs and specific application scenarios, which is not limited in embodiments of the present disclosure.

It may be understood that, if N fifth-type correlation vectors, N sixth-type correlation vectors or N seventh-type correlation vectors are generated in the foregoing steps, the fusion processing may further performed on the N first-type correlation vectors, the N second-type correlation vectors, the N third-type correlation vectors, the N fifth-type correlation vectors, the N sixth-type correlation vectors and the N seventh-type correlation vectors based on the above methods to generate the fourth fusion vector.

In some embodiments of the present disclosure, the fourth fusion vector may reflect the overall correlation degree between the medical data to be verified and the candidate document, thereby, calculation is performed on the fourth fusion vector through the softmax layer in the classification model, to generate the overall correlation degree between the medical data to be verified and the candidate document, i.e., the confidence degree of the medical data to be verified to the candidate document.

With the technical solution according to embodiments of the present disclosure, the medical data to be verified is represented in the form of SPO triple, and the medical data to be verified and the candidate document are processed by using the nature language processing model, so that the first feature vector corresponding to the entity in the medical data, the second feature vector corresponding to the attribute, the third feature vector corresponding to the attribute value, and the fourth feature vector corresponding to the candidate document are obtained, multiple methods are used to calculate the correlation between the entity and the candidate document, the correlation between the attribute and the candidate document, and the correlation between the attribute value and the candidate document to obtain the multiple first-type correlation vectors, second-type correlation vectors, and the third-type correlation vectors, and then, the fusion calculation is performed on the correlation vectors to determine the confidence degree of the medical data to the candidate document. Thus, through an end-to-end deep learning model, the correlation between medical data and the candidate document is calculated from multiple data dimensions of the medical data by using multiple methods, so that the correlation and difference between the medical data and the candidate document are accurately represented from multiple dimensions, and the end-to-end model may avoid accumulation of errors, thus further improving the accuracy of medical data verification.

In a possible implementation of the present disclosure, the documents related to the medical data to be verified may be retrieved from an authoritative medical database and determined as the candidate documents to reduce the number of candidate documents. In addition, the focus of calculating the correlation between the vectors varies with the calculation methods, which making different correlation vectors have different degrees of importance. Therefore, different calculation methods can be assigned different weights so as to further improve the accuracy of expressing the correlation between medical data and candidate document.

The medical data verification method provided in the embodiments of the present disclosure will be further described below with reference to FIG. 4.

Figure 4:
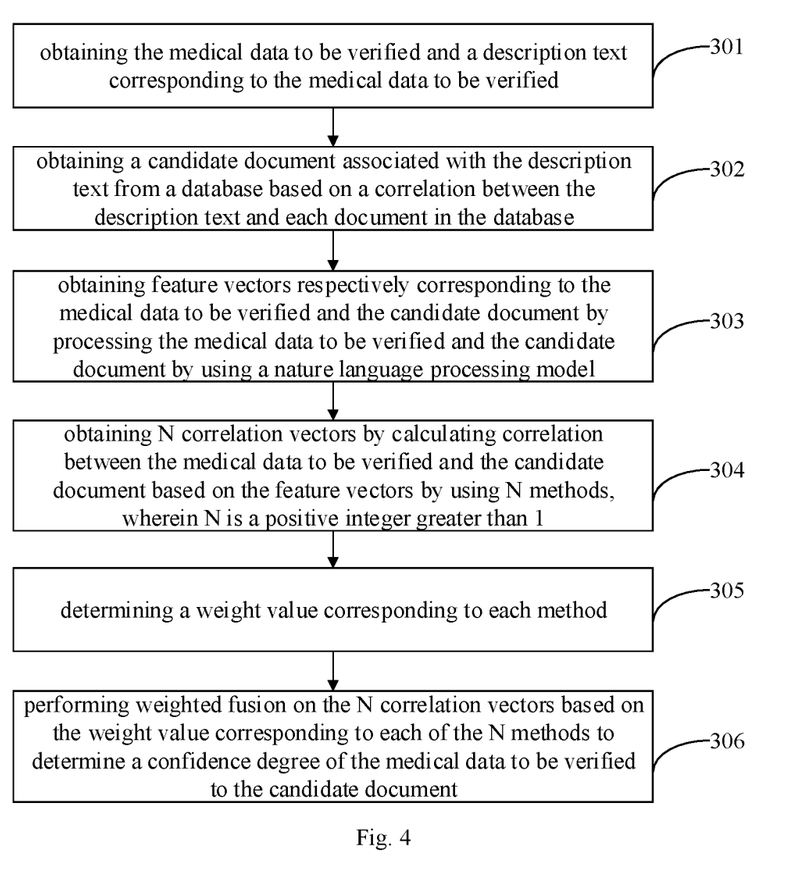
FIG. 4 is a flow chart of a medical data verification method according to an embodiment of the present disclosure.

FIG. 4 is a flow chart of a medical data verification method according to an embodiment of the present disclosure.

As illustrated in FIG. 4, the medical data verification method includes followings.

At block 301, medical data to be verified and a description text corresponding to the medical data to be verified are obtained.

The description text corresponding to the medical data to be verified may be an original text used when the medical data to be verified is extracted.

In some embodiments of the present disclosure, SPO triple data can be extracted from the original text of the patient's medical record, the medical certificate issued by the doctor, the medication record, etc. according to the actual application scenario to form the medical data to be verified, and the original text on which the medical data to be verified is extracted is determined as the corresponding description text.

For example, when the medical data verification method according to the embodiments of the present disclosure is applied to an auxiliary diagnosis scenario of a medical institution, a server obtains that a diagnosis result sent from a doctor client is "skin maculopapule on the body surface, which is diagnosed as measles", thus, the medical data to be verified extracted from the diagnosis result is <measles, symptom, skin maculopapular>, and the diagnosis result "skin maculopapular on the body surface, which is diagnosed as measles" can be determined as the corresponding description text.

At block 302, a candidate document associated with the description text is obtained from a database based on a correlation between the description text and each document in the database.

In some embodiments of the present disclosure, the description text may be used as a search keyword to search in the database, or keywords are extracted from the description text, and then used as search keywords to search in the database, to determine the correlation between the description text and each document in the database. And then, the documents in the database are sorted in a descending order according to the correlation between the description text and each document in the database. After that, a document with higher correlation with the description text than other documents is selected from the respective documents and determined as the candidate document. For example, M documents with relative high correlation with the description text are determined as the candidate documents, M is a positive integer, for example, M=1. Alternatively, a correlation threshold may be preset, and documents with a correlation greater than or equal to the correlation threshold may be determined as the candidate documents. Embodiments of the present disclosure do not limit this.

For example, the preset correlation threshold is 0.8, the description text is "skin maculopapular on the body surface, which is diagnosed as measles". The description text is taken as keywords for search in the database, and correlation between document A "Section 5 of [Infectious Diseases], 8th Edition, Measles: measles is a viral infectious disease caused by the measles virus, which belongs to the Class B infectious disease among the legal infectious diseases in our country. Its main clinical manifestations include fever, cough, runny nose and other catarrhal symptoms and conjunctivitis, and the characteristic manifestations are oral-measles koplik spots and skin maculopapule" and the description text is determined to be 0.9. And then, this document in section 5, Measles, in [Infectious Diseases], 8th Edition, may be determined as the candidate document.

It should be noted that, the database may be a pre-designated medical database, where various authoritative medical materials can be stored in the medical database, including books, magazines, and papers.

At block 303, feature vectors respectively corresponding to the medical data to be verified and the candidate document are obtained by processing the medical data to be verified and the candidate document by using a nature language processing model.

At block 304, N correlation vectors are obtained by calculating correlation between the medical data to be verified and the candidate document based on the feature vectors by using N methods, N is a positive integer greater than 1.

For the specific implementation process and principles of the foregoing steps at blocks 303-304, reference may be made to the detailed description of the foregoing embodiments, which is not repeated here.

At block 305, a weight value corresponding to each of the N methods is determined.

In some embodiments of the present disclosure, when multiple methods are used to calculate the correlation between the medical data and the candidate document, each calculation method has different focus on the difference and correlation between the vectors, resulting that the importance of each correlation vector to represent the correlation between medical data and candidate documents is different. Therefore, the weight value corresponding to each calculation method can be determined according to the importance for the correlation representation corresponding to each calculation method. For example, the N calculation methods may be a softmax operation, a subtraction operation, and a cosine operation, thus it is determined that a weight value of the cosine operation is greater than a weight value of the softmax operation, and the weight value of the softmax operation is greater than a weight value of the subtraction operation.

It should be noted that, the above examples are only illustrative, and should not be regarded as a limitation to the present disclosure. In actual use, the weight value corresponding to each calculation method can be determined according to actual needs and the characteristics of various calculation methods, which is not limited in the embodiment of the present disclosure.

At block 306, weighted fusion is performed on the N correlation vectors based on the weight value corresponding to each of the N methods, to determine a confidence degree of the medical data to the candidate document.

In some embodiments of the present disclosure, when the N correlation vectors are fused, a weighted sum of the N correlation vectors may be determined according to the weight value of the calculation method corresponding to each correlation vector, and the confidence degree of the medical data to be verified to the candidate document is determined according to the weighted sum of the N correlation vectors by using the softmax layer in the classification model.

With the technical solution according to embodiments of the present disclosure, the candidate document associated with the medical data to be verified is retrieved from the database based on the description text corresponding to medical data to be verified, and the medical data to be verified and the candidate document are processed by using the nature language processing model to obtain the feature vectors respectively corresponding to the medical data to be verified and the candidate document, and multiple correlation vectors are obtained by using multiple methods to calculate the correlation between the medical data to be verified and the candidate document based on the obtained feature vectors, and then, the weighted fusion is performed on the N correlation vectors based on the weight value corresponding to each calculation method to determine the confidence degree of the medical data to the candidate document. Thus, by retrieving documents related to the medical data to be verified from an authoritative medical database as the candidate documents, the number of candidate documents is reduced, and different weight values are assigned to respective correlation vectors according to the importance of each calculation method, to further improve the accuracy of the expressing the correlation between medical data and the candidate document, not only the accuracy of medical data verification is further improved, but also the computational complexity of medical data verification is reduced.

To implement the above embodiments, the present disclosure further proposes a medical data verification apparatus.

Figure 5:
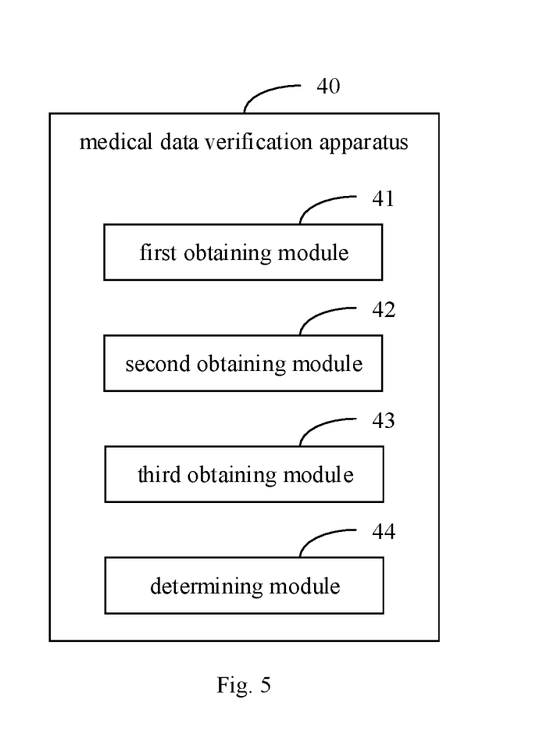
FIG. 5 is a block diagram illustrating a medical data verification apparatus according to an embodiment of the present disclosure.

FIG. 5 is a block diagram illustrating a medical data verification apparatus according to an embodiment of the present disclosure.

As illustrated in FIG. 5, the medical data verification apparatus 40 includes a first obtaining module 41, a second obtaining module 42, a third obtaining module 43, and a determining module 44.

The first obtaining module 41 is configure to obtain medical data to be verified and a candidate document.

The second obtaining module 42 is configure to obtain feature vectors respectively corresponding to the medical data to be verified and the candidate document by processing the medical data to be verified and the candidate document by using a nature language processing model.

The third obtaining module 43 is configure to obtain N correlation vectors by calculating correlation between the medical data to be verified and the candidate document based on the feature vectors by using N methods, wherein N is a positive integer greater than 1.

The determining module 44 is configure to determine a confidence degree of the medical data to be verified to the candidate document by performing fusion calculation on the N correlation vectors.

In actual use, the medical data verification apparatus provided by the embodiments of the present disclosure can be configured in any electronic device to execute the aforementioned medical data verification method.

With the technical solution according to embodiments of the present disclosure, the feature vectors respectively corresponding to the medical data to be verified and the candidate document are obtained by processing the medical data to be verified and the candidate document by using the nature language processing model, multiple correlation vectors are obtained by using multiple methods to calculate the correlation between the medical data to be verified and the candidate document based on the obtained feature vectors, and then, fusion calculation is performed on the correlation vectors to determine the confidence degree of the medical data to the candidate document. Thus, through an end-to-end deep learning model, the correlation between medical data and the candidate document is calculated by using multiple methods, so that the correlation and difference between the medical data and the candidate document are accurately represented from multiple dimensions, and the end-to-end model may avoid accumulation of errors, thus improving the accuracy of medical data verification.

In a possible implementation of the present disclosure, the medical data to be verified includes an entity, an attribute, and an attribute value. Correspondingly, the second obtaining module 42 includes a first obtaining unit.

The first obtaining unit is configured to obtain a first feature vector corresponding to the entity, a second feature vector corresponding to the attribute, a third feature vector corresponding to the attribute value, and a fourth feature vector corresponding to the candidate document.

Further, in another possible implementation of the present disclosure, the second obtaining module 42 further includes a second obtaining unit.

The second obtaining unit is configured to obtain at least one of: a fifth feature vector corresponding to the entity and the attribute, a sixth feature vector corresponding to the attribute and the attribute value, and a seventh feature vector corresponding to the entity and the attribute value.

Further, in yet another possible implementation of the present disclosure, the third obtaining module 43 includes a first calculation unit, a second calculation unit, and a third calculation unit.

The first calculation unit is configured to obtain N first-type correlation vectors by calculating correlation between the first feature vector and the fourth feature vector by respectively using the N methods.

The second calculation unit is configured to obtain N second-type correlation vectors by calculating correlation between the second feature vector and the fourth feature vector by respectively using the N methods.

The third calculation unit is configured to obtain N third-type correlation vectors by calculating correlation between the third feature vector and the fourth feature vector by respectively using the N methods.

Further, in still another possible implementation of the present disclosure, the determining module 44 includes a first fusion unit, a second fusion unit, a third fusion unit, and a first determining unit.

The first fusion unit is configured to obtain a first fusion vector by fusing the N first-type correlation vectors.

The second fusion unit is configured to obtain a second fusion vector by fusing the N second-type correlation vectors.

The third fusion unit is configured to obtain a first fusion unit, configured to obtain a third fusion vector by fusing the N third-type correlation vectors.

The first determining unit is configured to determine the confidence degree of the medical data to be verified to the candidate document by performing fusion calculation on the first fusion vector, the second fusion vector and the third fusion vector.

Further, in still another possible implementation of the present disclosure, the determining module 44 includes a fourth fusion unit and a second determining unit.

The fourth fusion unit is configured to fuse the N first-type correlation vectors, the N second-type correlation vectors and the N third-type correlation vectors to generate a fourth fusion vector.

The second determining unit is configured to determine the confidence degree of the medical data to be verified to the candidate document by performing calculation on the fourth fusion vector.

Further, in another possible implementation of the present disclosure, the determining module 44 includes a third determining unit and a fifth fusion unit.

The third determining unit is configured to determine a weight value corresponding to each of the N methods.

The fifth fusion unit is configured to perform weighted fusion on the N correlation vectors based on the weight value corresponding to each of the N methods.

Further, in yet another possible implementation of the present disclosure, the first obtaining module 41 includes a third obtaining unit and a fourth obtaining unit.

The third obtaining unit is configured to obtain the medical data to be verified and a description text corresponding to the medical data to be verified.

The fourth obtaining unit is configured to obtain a candidate document associated with the description text from a database based on a correlation between the description text and each document in the database.

It should be noted that the foregoing explanations of the embodiments of the medical data verification method illustrated in FIG. 1, FIG. 3, and FIG. 4 are also applicable to the medical data verification apparatus 40 of this embodiment, and will not be repeated here.

With the technical solution according to embodiments of the present disclosure, the medical data to be verified is represented in the form of SPO triple, and the medical data to be verified and the candidate document are processed by using the nature language processing model, so that the first feature vector corresponding to the entity in the medical data, the second feature vector corresponding to the attribute, the third feature vector corresponding to the attribute value, and the fourth feature vector corresponding to the candidate document are obtained, multiple methods are used to calculate the correlation between the entity and the candidate document, the correlation between the attribute and the candidate document, and the correlation between the attribute value and the candidate document to obtain the multiple first-type correlation vectors, second-type correlation vectors, and the third-type correlation vectors, and then, the fusion calculation is performed on the correlation vectors to determine the confidence degree of the medical data to the candidate document. Thus, through an end-to-end deep learning model, the correlation between medical data and the candidate document is calculated from multiple data dimensions of the medical data by using multiple methods, so that the correlation and difference between the medical data and the candidate document are accurately represented from multiple dimensions, and the end-to-end model may avoid accumulation of errors, thus further improving the accuracy of medical data verification.

According to embodiments of the present disclosure, the present disclosure further provides an electronic device and a computer-readable storage medium.

Figure 6:
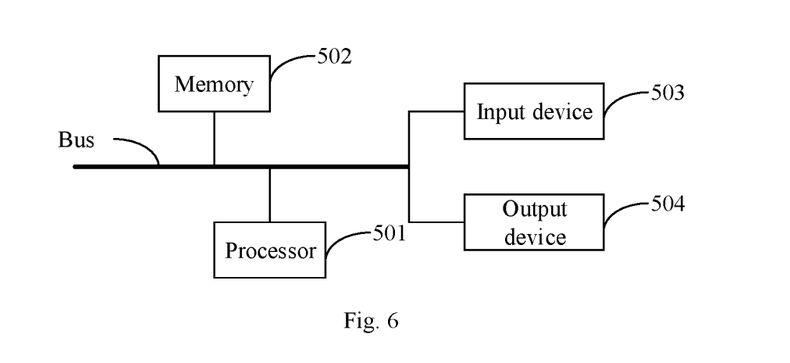
FIG. 6 is a schematic diagram illustrating an electronic device for implementing a medical data verification method according to an embodiment of the present disclosure.

FIG. 6 is a schematic diagram of an electronic device for implementing the medical data verification method according to an embodiment of the present disclosure. The electronic device is intended to represent various forms of digital computers, such as a laptop computer, a desktop computer, a workstation, a personal digital assistant, a server, a blade server, a mainframe computer, and other suitable computers. The electronic device can also represent various forms of mobile devices, such as personal digital processing, a cellular phone, a smart phone, a wearable device, and other similar computing devices. The components shown herein, their connections and relationships, and their functions are merely examples, and are not intended to limit the implementation of the present disclosure described and/or required herein.

As illustrated in FIG. 6, the electronic device includes one or more processors 501, a memory 502, and interfaces for connecting various components. The interfaces include a high-speed interface and a low-speed interface. The various components are connected to each other using different buses, and can be installed on a common mainboard or installed in other ways as needed. The processor may process instructions executed in the electronic device, including instructions stored in or on the memory to display graphical information of the GUI on an external input/output device (such as a display device coupled to an interface). In other embodiments, if necessary, multiple processors and/or multiple buses can be used together with multiple memories. Similarly, multiple electronic devices can be connected, and each device provides some necessary operations (for example, as a server array, a group of blade servers, or a multi-processor system). In FIG. 6, one processor 501 is taken as an example.

The memory 502 is the non-transitory computer-readable storage medium provided by the present disclosure. The memory stores instructions executable by the at least one processor, so that the at least one processor executes the medical data verification method provided in the present disclosure. The non-transitory computer-readable storage medium of the present disclosure stores computer instructions, and the computer instructions are used to cause a computer to execute the medical data verification method provided by the present disclosure.

As a non-transitory computer-readable storage medium, the memory 502 can be used to store non-transitory software programs, non-transitory computer-executable programs and modules, such as program instructions/modules (for example, the first obtaining module 41, the second obtaining module 42, the third obtaining module 43, and the determining module 44 shown in FIG. 5) corresponding to the medical data verification method in the embodiments of the present disclosure. The processor 501 executes various functional applications and data processing of the server by running the non-transitory software programs, instructions, and modules stored in the memory 502, that is, realizes the medical data verification method in the foregoing method embodiment.

The memory 502 may also include a program storage area and a data storage area. The program storage area may store an operating system and an application program required by at least one function. The data storage area may store data created according to the use of the electronic device for the medical data verification method, etc. In addition, the memory 502 may include a high-speed random access memory, and may also include a non-transitory memory, such as at least one magnetic disk storage device, a flash memory device, or other non-transitory solid-state storage devices. In some embodiments, the memory 502 may optionally include memories remotely provided with respect to the processor 501, and these remote memories may be connected to an electronic device for implementing the medical data verification method. Examples of the aforementioned networks include, but are not limited to, the Internet, intranets, local area networks, mobile communication networks, and combinations thereof.

The electronic device for implementing the medical data verification method may further include an input device 503 and an output device 504. The processor 501, the memory 502, the input device 503, and the output device 504 may be connected by a bus or in other ways. In FIG. 6, the connection via a bus is taken as an example.

The input device 503 can receive input numeric or character information, and generate key signal input related to the user settings and function control of the electronic device for the medical data verification method, such as input devices like a touch screen, a keypad, a mouse, a trackpad, a touchpad, a pointing stick, one or more mouse buttons, a trackball, a joystick, etc. The output device 404 may include a display device, an auxiliary lighting device (for example, a light-emitting diode (LED)), a tactile feedback device (for example, a vibration motor), and the like. The display device may include, but is not limited to, a liquid crystal display (LCD), a LED display, and a plasma display. In some embodiments, the display device may be a touch screen.

Various implementations of the systems and technologies described herein can be implemented in a digital electronic circuit system, an integrated circuit system, an application-specific ASIC (application-specific integrated circuit), computer hardware, firmware, software, and/or combinations thereof. These various embodiments may include: being implemented in one or more computer programs, the one or more computer programs may be executed and/or interpreted on a programmable system including at least one programmable processor, the programmable processor may be a dedicated or general-purpose programmable processor that can receive data and instructions from a storage system, at least one input device, and at least one output device, and transmit the data and instructions to the storage system, the at least one input device, and the at least one output device.

These computing programs (also called programs, software, software applications, or codes) include machine instructions for the programmable processors, and high-level processes and/or object-oriented programming languages, and/or assembly/machine language may be utilized to implement these calculation programs. As used herein, the terms "machine-readable medium" and "computer-readable medium" refer to any computer program product, apparatus, and/or device used to provide machine instructions and/or data to the programmable processor, such as, magnetic disks, optical disks, memory, programmable logic devices (PLD), including machine-readable media that receive machine instructions as machine-readable signals. The term "machine-readable signal" refers to any signal used to provide machine instructions and/or data to a programmable processor.

In order to provide interaction with the user, the systems and techniques described herein may be implemented on a computer having a display device (for example, a Cathode Ray Tube (CRT) or Liquid Crystal Display (LCD) monitor) for displaying information to the user; and a keyboard and pointing device (such as a mouse or trackball) through which the user can provide input into a computer. Other kinds of apparatuses may also be used to provide interaction with the user. For example, the feedback provided to the user may be any form of sensory feedback (for example, visual feedback, auditory feedback, or haptic feedback); and input from the user may be received in any form (including acoustic input, voice input, or tactile input).

The systems and technologies described herein can be implemented in a computing system including background components (for example, as a data server), a computing system including middleware components (for example, an application server), or a computing system including front-end components (for example, a user computer with a graphical user interface or a web browser, through which the user can interact with the implementation of the systems and technologies described herein), or a computer system including any combination of such background components, middleware components, and front-end components. The components of the system may be interconnected by any form or medium of digital data communication (such as, a communication network). Examples of communication networks include: a local area network (LAN), a wide area network (WAN), and the Internet.

The computer system may include clients and servers. The client and server are generally remote from each other and typically interact through a communication network. The client-server relation is generated by computer programs running on the respective computers and having a client-server relation with each other. The server may be a cloud server, also known as a cloud computing server or a cloud host, which is a host product in the cloud computing service system, to solve defects of difficult management and weak business scalability in the traditional physical host and VPS (Virtual Private Server) service.

With the technical solution according to embodiments of the present disclosure, the feature vectors respectively corresponding to the medical data to be verified and the candidate document are obtained by processing the medical data to be verified and the candidate document by using the nature language processing model, multiple correlation vectors are obtained by using multiple methods to calculate the correlation between the medical data to be verified and the candidate document based on the obtained feature vectors, and then, fusion calculation is performed on the correlation vectors to determine the confidence degree of the medical data to the candidate document. Thus, through an end-to-end deep learning model, the correlation between medical data and the candidate document is calculated by using multiple methods, so that the correlation and difference between the medical data and the candidate document are accurately represented from multiple dimensions, and the end-to-end model may avoid accumulation of errors, thus improving the accuracy of medical data verification.

It should be understood that the various forms of flows shown above can be used to reorder, add, or delete steps. For example, the steps disclosed in the present application can be executed in parallel, sequentially, or in different orders. As long as the desired results of the technical solutions disclosed in the present disclosure can be achieved, there is no limitation herein.

The foregoing specific embodiments do not constitute a limitation on the protection scope of the present disclosure. It should be understood by those skilled in the art that various modifications, combinations, sub-combinations, and substitutions may be made according to design requirements and other factors. Any modification, equivalent replacement and improvement made within the spirit and principle of the present disclosure shall be included in the protection scope of the present disclosure.

What is claimed is:

1. A medical data verification method, comprising:
    obtaining medical data to be verified and a candidate document, wherein the medical data to be verified comprises an entity, an attribute, and an attribute value;
    obtaining a first feature vector corresponding to the entity, a second feature vector corresponding to the attribute, a third feature vector corresponding to the attribute value, and a fourth feature vector corresponding to the candidate document, by processing the medical data to be verified and the candidate document by using a natural language processing model;
    obtaining N first-type correlation vectors by calculating correlation between the first feature vector and the fourth feature vector by respectively using N methods, wherein N is a positive integer greater than 1;
    obtaining N second-type correlation vectors by calculating correlation between the second feature vector and the fourth feature vector by respectively using the N methods;
    obtaining N third-type correlation vectors by calculating correlation between the third feature vector and the fourth feature vector by respectively using the N methods; and
    determining a confidence degree of the medical data to be verified to the candidate document by performing fusion calculation on the correlation vectors.

2. The method according to claim 1, wherein, obtaining the feature vectors respectively corresponding to the medical data to be verified and the candidate document further comprises:
    obtaining at least one of: a fifth feature vector corresponding to the entity and the attribute, a sixth feature vector corresponding to the attribute and the attribute value, and a seventh feature vector corresponding to the entity and the attribute value.

3. The method according to claim 1, wherein determining the confidence degree of the medical data to be verified to the candidate document by performing fusion calculation on the correlation vectors comprises:
    obtaining a first fusion vector by fusing the N first-type correlation vectors;
    obtaining a second fusion vector by fusing the N second-type correlation vectors;
    obtaining a third fusion vector by fusing the N third-type correlation vectors; and
    determining the confidence degree of the medical data to be verified to the candidate document by performing fusion calculation on the first fusion vector, the second fusion vector and the third fusion vector.

4. The method according to claim 1, wherein determining the confidence degree of the medical data to be verified to the candidate document by performing fusion calculation on the correlation vectors comprises:
fusing the N first-type correlation vectors, the N second-type correlation vectors and the N third-type correlation vectors to generate a fourth fusion vector; and
determining the confidence degree of the medical data to be verified to the candidate document by performing calculation on the fourth fusion vector.

5. The method according to claim 1, wherein performing the fusion calculation on the correlation vectors comprises:
determining a weight value corresponding to each of the N methods; and
performing weighted fusion on the correlation vectors based on the weight value corresponding to each of the N methods.

6. The method according to claim 1, wherein obtaining the medical data to be verified and the candidate document comprises:
obtaining the medical data to be verified and a description text corresponding to the medical data to be verified; and
obtaining a candidate document associated with the description text from a database based on a correlation between the description text and each document in the database.

7. An electronic device, comprising:
at least one processor; and
a memory communicatively couple to the at least one processor;
wherein, the memory has instructions executable by the at least one processor stored thereon that, when executed by the at least one processor, cause the at least one processor to perform a medical data verification method, comprising:
obtaining medical data to be verified and a candidate document, wherein the medical data to be verified comprises an entity, an attribute, and an attribute value;
obtaining a first feature vector corresponding to the entity, a second feature vector corresponding to the attribute, a third feature vector corresponding to the attribute value, and a fourth feature vector corresponding to the candidate document, by processing the medical data to be verified and the candidate document by using a natural language processing model;
obtaining N first-type correlation vectors by calculating correlation between the first feature vector and the fourth feature vector by respectively using N methods, wherein N is a positive integer greater than 1;
obtaining N second-type correlation vectors by calculating correlation between the second feature vector and the fourth feature vector by respectively using the N methods;
obtaining N third-type correlation vectors by calculating correlation between the third feature vector and the fourth feature vector by respectively using the N methods; and
determining a confidence degree of the medical data to be verified to the candidate document by performing fusion calculation on the correlation vectors.

8. The electronic device according to claim 7, wherein, obtaining the feature vectors respectively corresponding to the medical data to be verified and the candidate document further comprises:
obtaining at least one of: a fifth feature vector corresponding to the entity and the attribute, a sixth feature vector corresponding to the attribute and the attribute value, and a seventh feature vector corresponding to the entity and the attribute value.

9. The electronic device according to claim 7, wherein determining the confidence degree of the medical data to be verified to the candidate document by performing fusion calculation on the correlation vectors comprises:
obtaining a first fusion vector by fusing the N first-type correlation vectors;
obtaining a second fusion vector by fusing the N second-type correlation vectors;
obtaining a third fusion vector by fusing the N third-type correlation vectors; and
determining the confidence degree of the medical data to be verified to the candidate document by performing fusion calculation on the first fusion vector, the second fusion vector and the third fusion vector.

10. The electronic device according to claim 7, wherein determining the confidence degree of the medical data to be verified to the candidate document by performing fusion calculation on the correlation vectors comprises:
fusing the N first-type correlation vectors, the N second-type correlation vectors and the N third-type correlation vectors to generate a fourth fusion vector; and
determining the confidence degree of the medical data to be verified to the candidate document by performing calculation on the fourth fusion vector.

11. The electronic device according to claim 7, wherein performing the fusion calculation on the correlation vectors comprises:
determining a weight value corresponding to each of the N methods; and
performing weighted fusion on the correlation vectors based on the weight value corresponding to each of the N methods.

12. The electronic device according to claim 7, wherein obtaining the medical data to be verified and the candidate document comprises:
obtaining the medical data to be verified and a description text corresponding to the medical data to be verified; and
obtaining a candidate document associated with the description text from a database based on a correlation between the description text and each document in the database.

13. A non-transitory computer-readable storage medium having computer instructions stored thereon, wherein the computer instructions are configured to cause a computer to perform a medical data verification method, comprising:
obtaining medical data to be verified and a candidate document, wherein the medical data to be verified comprises an entity, an attribute, and an attribute value;
obtaining a first feature vector corresponding to the entity, a second feature vector corresponding to the attribute, a third feature vector corresponding to the attribute value, and a fourth feature vector corresponding to the candidate document, by processing the medical data to be verified and the candidate document by using a natural language processing model;
obtaining N first-type correlation vectors by calculating correlation between the first feature vector and the fourth feature vector by respectively using N methods, wherein N is a positive integer greater than 1;

obtaining N second-type correlation vectors by calculating correlation between the second feature vector and the fourth feature vector by respectively using the N methods;

obtaining N third-type correlation vectors by calculating correlation between the third feature vector and the fourth feature vector by respectively using the N methods; and determining a confidence degree of the medical data to be verified to the candidate document by performing fusion calculation on the correlation vectors.

14. The storage medium according to claim 13, wherein, obtaining the feature vectors respectively corresponding to the medical data to be verified and the candidate document further comprises:

obtaining at least one of: a fifth feature vector corresponding to the entity and the attribute, a sixth feature vector corresponding to the attribute and the attribute value, and a seventh feature vector corresponding to the entity and the attribute value.

* * * * *